US00PP19797P2

(12) United States Plant Patent

Van Spronsen

(10) Patent No.: US PP19,797 P2

(45) Date of Patent: Mar. 3, 2009

(54) *CHRYSANTHEMUM* PLANT NAMED 'POWER PURPLE'

(50) Latin Name: *Chrysanthemum ×morifolium*
Varietal Denomination: Power Purple

(75) Inventor: Simon Van Spronsen, Niagra on the Lake (CA)

(73) Assignee: Willy's Greenhouse Ltd., Niagara on the Lake (CA)

( * ) Notice: Subject to any disclaimer, the term of this patent is extended or adjusted under 35 U.S.C. 154(b) by 0 days.

(21) Appl. No.: 12/011,815

(22) Filed: Jan. 30, 2008

(51) Int. Cl.
*A01H 5/00* (2006.01)

(52) U.S. Cl. ..... Plt./286

(58) Field of Classification Search ..... Plt./286
See application file for complete search history.

*Primary Examiner*—Annette H Para

(74) *Attorney, Agent, or Firm*—Penny J. Aguirre

(57) ABSTRACT

A new cultivar of *Chrysanthemum,* 'Power Purple', characterized by it's early and free flowering habit, its daisy-type inflorescences with dark purple ray florets and bright yellow disk florets opening from deep purple buds, its vigorous freely branched growth habit, its small leaved dark green foliage and its uniform, rounded and outward spreading plant habit.

2 Drawing Sheets

Botanical classification: *Chrysanthemum×morifolium.*
Variety denomination: 'Power Purple'.

BACKGROUND OF THE INVENTION

The present invention relates to a new and distinct cultivar of *chrysanthemum* plant, botanically known as *Chrysanthemum×morifolium* 'Power Purple'and hereinafter by its cultivar name, 'Power Purple'.

The new *chrysanthemum* 'Power Purple' was discovered by the inventor as a naturally occurring branch mutation of the *Chrysanthemum* cultivar 'Dark Cherie' (U.S. Plant Pat. No. 8,830) in July 2007 in Niagara on the Lake, Ontario, Canada.

Asexual reproduction of the new cultivar was first accomplished via stem cuttings in July 2007 in Niagara on the Lake, Ontario, Canada. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish by 'Power Purple' as unique from all other varieties of *Chrysanthemums* known to the inventor.

1. The inflorescences of 'Power Purple' have dark purple ray florets with bright yellow disk florets that open from deep purple buds.
2. 'Power Purple' is early flowering with daisy-type inflorescences about 3.8 cm in diameter when grown as a spray pot.
3. 'Power Purple' has a freely branched, uniform, rounded and outward plant habit.
4. 'Power Purple' has a uniform flowering response.
5. 'Power Purple' has small leaved dark green foliage.
6. 'Power Purple' is a vigorous grower.

In comparison to the parent plant, 'Dark Cherie', 'Power Purple' has ray florets that are darker and more purple in color than the ray florets of 'Dark Cherie' which are red-purple in color. Based on its growth habit, flowering response and flower type, 'Power Purple' can be most closely compared to 'Soft Cherie' (U.S. Plant Pat. No. 8,802) which has light purple colored ray florets, 'Apricot Cherie' (U.S. Plant Pat. No. 12,691) which has soft pink to tan colored ray florets and 'Power Yellow' (U.S. Plant Pat. No. 18,175) which has yellow ray florets. Based on flower color and flower type, 'Dark Cherie' can also be compared to 'Desiree' (U.S. Plant Pat. No. 7,500), which has dark purple colored inflorescence buds, however 'Desiree' has ray florets that are lighter purple in color, smaller inflorescences, and a slower flowering response.

BRIEF DESCRIPTION OF THE DRAWINGS

The accompanying colored photographs illustrate the overall appearance and distinct characteristics of the new *Chrysanthemum,* 'Power Purple'. The photographs were taken of plants grown in a 5-inch pan pot planted with 3 rooted cuttings and grown under greenhouse conditions for 10 weeks.

Figure 1:
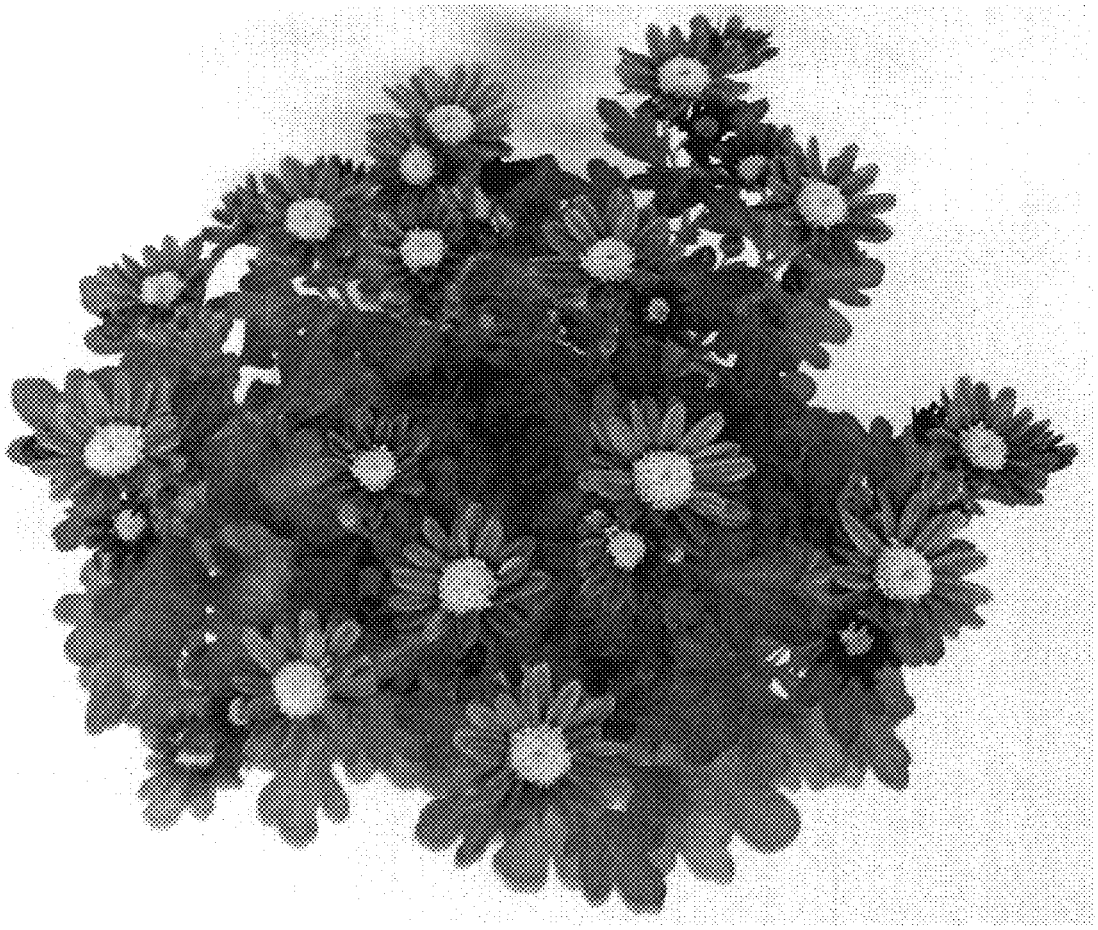
FIG. 1 is a photograph that provides a top view of a typical plant of 'Power Purple' in bloom when grown as a spray-type.
Figure 2:
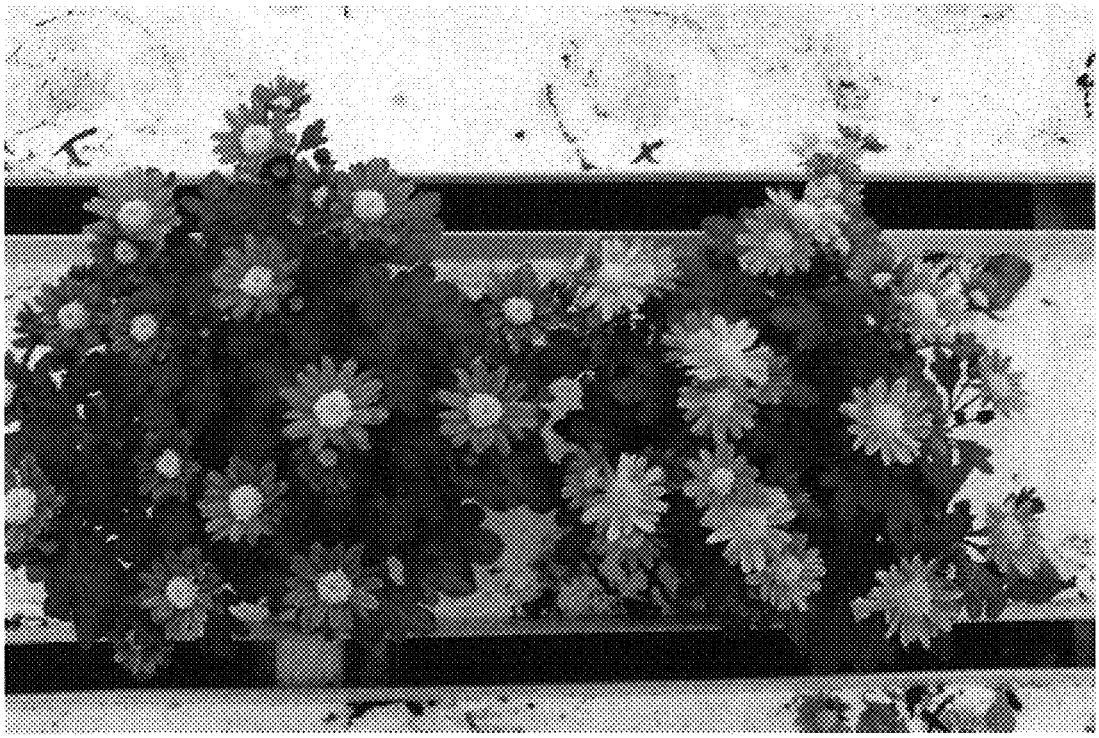

The photograph in FIG. 2 is a top view and provides a comparison between 'Power Purple' (left) and 'Dark Cherie' (right).

The colors in the photographs are as close as possible with the photographic and printing technology utilized. The color values cited in the detailed botanical description accurately describe the colors of the new *Chrysanthemum.*

DETAILED BOTANICAL DESCRIPTION

The following is a detailed description of plants of the new cultivar as grown in a 5-inch pan pot planted with 3 single pinched rooted cuttings and grown under greenhouse conditions at an average temperature of 65° F. for 10 weeks. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Commercial classification.*—Daisy-type spray pot *Chrysanthemum.*

*Flowering response.*—Early blooming, flowering occurs after short day treatment in about 52 days in spring, summer and fall and 56 days in winter.

*Plant type.*—Herbaceous, grown as a potted *Chrysanthemum* as a spray-type.

*Plant habit.*—Uniform, compact, mounded plant habit.

*Height and spread.*—Reaches about 15 cm in height and 24 cm in width when grown under the conditions tested under greenhouse conditions.

*Diseases resistance.*—No susceptibility or resistance to diseases common to *Chrysanthemum* has been observed under commercial greenhouse productions.

*Root description.*—Fibrous.

Growth and propagation:

*Propagation.*—Terminal stem cuttings.

*Time to root.*—About 8 days at 20° C.

*Production.*—Rooted cuttings grown on at 65° F. finish in a 5-inch pan pot in 8 weeks.

*Growth rate.*—Vigorous.

Stem description:

*Stem color.*—138B with pubescence of 138B and 138C.

*Stem strength.*—Strong and flexible.

*Stem surface.*—Pubescent.

*Branching habit and quantity.*—Freely branched, about 5 branches per stem after removal of the apical meristem (pinching).

*Lateral branch size.*—About 10 cm in length and about 3.5 mm in width.

*Internode length.*—Lateral branches in a whorl from pinched node at base.

Foliage description:

*Leaf division.*—Simple.

*Leaf shape.*—Blade is broadly ovate with narrowing towards base.

*Leaf base.*—Limb base is cuneate, narrow base is truncate.

*Leaf apex.*—Rounded to broadly acute and mucronate.

*Leaf margin.*—Matures to trifid to five-lobed with apex of lobes rounded with mucrunate tips.

*Leaf texture.*—Upper surface slightly pubescent, lower surface pubescent.

*Leaf venation.*—Palmate, upper surface and lower surface 138B to 138C.

*Leaf attachment.*—Sessile.

*Leaf arrangement.*—Alternate.

*Leaf number.*—Average of 20 per lateral branch.

*Leaf internode length.*—Average of 1.2 cm.

*Leaf color.*—Young and mature foliage upper surface; between 137A and 138A, young and mature foliage lower surface; 138B.

*Leaf size* (*fully expanded*).—Average of 4.9 cm in length and 3 cm in width (expanded blade portion is an average of 3.3 cm in length).

*Fragrance of foliage.*—Fragrant if bruised.

Flower description:

General description:

*Inflorescence type.*—Composite, daisy form with oblong shaped ray florets and disk flowers arranged acropetally on a capitulum, inflorescences typically borne in compound corymbs.

*Postproduction longevity.*—Conditions dependent, inflorescences maintain good color and substance for about 2 weeks in an interior environment.

*Fragrance.*—Faint.

*Quantity of inflorescences.*—Average of 10 per lateral stem, about 150 per plant produced from 3 cuttings.

*Inflorescence size.*—About 1 cm in depth and 3.8 cm in diameter, diameter of disk about 1 cm.

*Inflorescence buds.*—About 1 cm in depth and 8 mm in diameter, globose becoming ovate in shape prior to opening, a color between N79B to N79C in color with phyllaries 138A to 138B.

*Peduncle.*—Strong, flexible, held from upright to an angle of 30° to vertical, surface is pubescent, an average of 2.5 cm in length and 2 mm in width, 138A in color with pubescence of 138B and 138C.

*Involucral bracts* (*phyllaries*).—Arranged in two layers, 138A to 138B in color with translucent margins, about 3.5 mm in length and 1.5 mm in width, surface is glandular and pubescence.

*Receptacle.*—About 4 mm in diameter and 3 mm in depth, 144A to 144B in color.

Ray florets (capitulate):

*Number.*—Average of 22.

*Arrangement.*—In 2 rows.

*Shape.*—Elongated oblong.

*Aspect.*—Emerge vertical and open to primarily horizontal when fully open.

*Size.*—Average of 1.5 cm in length and 5 mm in width.

*Petal apex.*—Rounded with one or two notches.

*Petal base.*—Cuneate.

*Petal margins.*—Entire.

*Petal texture.*—Glabrous on upper and lower surface and ridged.

*Petal color.*—Opening upper and lower surface; N77C with base with N79A, fully open upper and lower surface 77B to 77C suffused with N77B, base surrounded pistil 144D.

Disk Florets (perfect):

*Arrangement.*—Massed in center of receptacle.

*Quantity.*—Average of 95.

*Shape.*—Tubular.

*Size.*—About 5 mm in length and about 1.5 mm in width.

*Color.*—Immature 1C, mature 2A to 2C.

Reproductive organs:

*Presence.*—Disk flowers are perfect, ray flowers are carpellate.

*Gynoecium.*—1 Pistil per disk and ray floret, 4 mm in length, style color 154D, stigma color 12A.

*Androcoecium.*—5 stamens per disk floret, fused into tube surrounding style, anthers are translucent and color 154D, pollen is moderate in quantity and 17B in color.

*Seed.*—Seed production has not been observed under the conditions tested.

It is claimed:

1. A new and distinct cultivar of *Chrysanthemum* plant named 'Power Purple' as herein illustrated and described.

* * * * *